US005628781A

United States Patent [19]
Williams et al.

[11] Patent Number: 5,628,781

[45] Date of Patent: May 13, 1997

[54] IMPLANT MATERIALS, METHODS OF TREATING THE SURFACE OF IMPLANTS WITH MICROVASCULAR ENDOTHELIAL CELLS, AND THE TREATED IMPLANTS THEMSELVES

[75] Inventors: Stuart K. Williams; Bruce E. Jarrell, both of Tucson, Ariz.

[73] Assignee: Thomas Jefferson University, Philadelphia, Pa.

[21] Appl. No.: 953,474

[22] Filed: Sep. 29, 1992

Related U.S. Application Data

[63] Continuation-in-part of Ser. No. 880,559, May 8, 1992, abandoned, and Ser. No. 725,950, Jun. 27, 1991, Pat. No. 5,230,693, which is a continuation of Ser. No. 244,496, Sep. 12, 1988, abandoned, which is a division of Ser. No. 742,086, Jun. 6, 1985, Pat. No. 4,820,626, said Ser. No. 880,559, is a division of Ser. No. 666,475, Mar. 6, 1991, Pat. No. 5,131,907, which is a continuation of Ser. No. 848,453, Apr. 4, 1986, abandoned, which is a continuation-in-part of Ser. No. 742,086.

[51] Int. Cl.$^6$ ............................................. A61F 2/06
[52] U.S. Cl. ............................. 623/1; 623/11; 435/371; 424/93.21
[58] Field of Search ....................... 623/1, 11; 935/70, 935/71; 435/240.2

[56] References Cited

U.S. PATENT DOCUMENTS

| 4,678,468 | 7/1987 | Hiroyoshi | 623/1 |
|---|---|---|---|
| 4,787,900 | 11/1988 | Yannas | 623/1 |
| 4,932,964 | 6/1990 | Bittman et al. | 623/1 |
| 4,970,298 | 11/1990 | Silver | 128/DIG. 8 |
| 5,171,261 | 12/1992 | Noishiki et al. | 623/1 |
| 5,336,615 | 8/1994 | Bell et al. | 623/1 |

OTHER PUBLICATIONS

Belden et al., "Endothelial Cell Seeding of Small–Diameter Vascular Grafts", *Trans. Am. Soc. Artif. Intern. Organs* 1982, 28, 173–177.

Berger, et al., "Healing of Arterial Prostheses in Man: It's Incompleteness", *Ann. Surg.* 1972, 175, 118–127.

Burkel et al., "Fate of Knitted Dacron Velour Vascular Grafts Seeded with Enzymatically Derived Autologous Canine Endothelium", *Trans. Am. Soc. Artif. Intern. Organs* 1982, 28, 178–182.

Dilley et al., "Endothelial Seeding of Vascular Prostheses", *Biology of Endothelial Cells*, pp. 401–411, Jaffe ed., The Hague: Martinus Nijhoff, 1984.

Eskin et al., "Behavior of Endothelial Cells cultured on Silastic and Dacron Velour Under Flow conditionsi In Vitro: Implications for Prelining Vascular Grafts wit Cells", *Artificial Organs* 1983, 7(1), 31–37.

Fishman, "Endothelium: A Distributed Organ of Diverse Capabilities", *Annals of New York Academy of Sciences* 1982, 1–8; Sauvage et al., Interspecies Healing of Porous Arterial Prostheses, *Arch Surg.* 1974, 109, 698–705.

Glassberg et al., "Cultured Endothelial Cells Derived From Human Iliac Arteries", *In Vitro* 1982, 18, 859–866.

Graham et al., "Cultured Autogenous Endothelial Cell Seeding of Vascular Prosthetic Grafts", *Surg Forum* 1979, 30, 204–206.

Graham et al., "Expanded Polytetrafluoroethylene Vascular Prostheses Seeded with Enzymatically Derived and Cultured Canine Endothelial Cells", *Surgery* 1982, 91(5), 550–559.

(List continued on next page.)

*Primary Examiner*—Robert A. H. Clarke
*Attorney, Agent, or Firm*—Woodcock Washburn Kurtz Mackiewicz & Norris

[57] ABSTRACT

Implant materials having porosity are provided by the present invention. Methods for treating a synthetic or naturally occurring implant, such as a vascular graft, intended for implantation in a human patient are also provided comprising obtaining human microvascular fat tissue, homogenizing the fat tissue to provide a cellular slurry, and applying the cellular slurry onto said implant to provide at least 50% confluence of said cells on the surface and/or within the pores of the implant.

6 Claims, 3 Drawing Sheets

FLOW-THROUGH

OTHER PUBLICATIONS

Herring et al., "A Single Staged Technique for Seeding Vascular Grafts with Autogenous Endothelium", *Surgery* 1978, 84, 498–504.

Herring et al., "Seeding Arterial Prostheses with Vascular Endothelium", *Ann. Surg.* 1979, 190(1), 84–90.

Hess et al., "The Endothelialization Process of a Fibrous Polyurethane Microvascular Prostheses After Implantation in the Abdominal Aorta of the Rat", *Journal of Cardiovascular Surgery* 1983, 24(5), 516–524.

Ishihara et al., "Occurrence and Significance of Endothelial Cells in Implanted Porcine Bioprosthetic Valves", *American Journal of Cardiology* 1981, 48, 443–454.

Ives et al., "The Importance of Cell Origin and Substrate in the kinetics of Endothelial cell Alignment in Response to Steady Flow", *Trans. Am. Soc. Artif. Intern Organs* 1983, 29, 269–274.

Jaffe et al., "Synthesis of Antihemophilia Factor Antigen by Cultured Human Endothelial Cells", *J. Clin. Invest.* 1973, 55, 2757–2764.

Jaffe et al., "Culture of Human Endothelial Cells Derived From Umbilical Veins", *J. Clin. Invest.* 1973, 52, 2745–2756.

Jarrell et al., "Human Adult Endothelial Cell Growth in Culture", *Journal of Vascular Surgery* 1984, I(6), 757–764.

Lewis, "Endothelium in Tissue Culture", *Am. J. Anat.* 1922, 30, 39–59.

Madri and Williams, "Capillary Endothelial Cell Cultures: Phenotypic Modulation by Matrix Components", *J. Cell Biol.* 1983, 97, 153.

Nichols et al., "Increased Adherence of Vascular Endothelial Cells to Biomer Precoated with Extracellular Matrix", *Trans. Am. Soc. Artif. Intern Organs* 1981, 28, 208–212.

*Plastics*, 85, Proceedings of the SPE 43rd Annual Technical Conference and Exhibition pp. 685–688 (1985).

Sharefkin et al., "Early Normalization of Platelet Survival by Endothelial Seeding of Dacron Arterial Prostheses in Dogs", *Surgery* 1982, 92, 385–393.

Sauvage et al., "Interspecies Healing of Porous Arterial Prostheses", *Arch. Surg.* 1974, 109, 698–705.

Stanley et al., "Enhanced Patency of Small Diameter Externally Supported Dacron Iliofemoral Grafts Seeded with Endothelial Cells", *Surgery* 1982, 92, 994–1005.

Watkins et al., "Adult Human Saphenous Vein Endothelial Cells: Assessment of Their Reproductive Capacity for Use in Endothelial Seeding of Vascular Prostheses", *J. Surg. Res.* 1984, 36, 588–596.

Wesolow, "The Healing of Arterial Prostheses—The State of the Art", *Thorac. Cardiovasc. Surgeon* 1982, 30, 196–208.

Kern et al., "Isolation and Culture of Microvascular Endothelium from Human Adipose Tissue", *J. Clin. Invest.* 1983, 71, 1822–1829.

Dichek et al., "Seedling of Intravascular Stents with Genetically Engineered Endothelial Cells," *Circulation* 80 (5): 1347–1352 (1989).

GRAVITY

FLOW-THROUGH

IMPLANT MATERIALS, METHODS OF TREATING THE SURFACE OF IMPLANTS WITH MICROVASCULAR ENDOTHELIAL CELLS, AND THE TREATED IMPLANTS THEMSELVES

CROSS-REFERENCE TO RELATED APPLICATIONS

This application is a continuation-in-part of U.S. Ser. No. 725,950 filed Jun. 27, 1991, now U.S. Pat. No. 5,230,693, which is a continuation of U.S. Ser. No. 07/244,496, filed Sep. 12, 1988, now abandoned, which is a divisional of U.S. Ser. No. 06/742,086 filed Jun. 6, 1985, now U.S. Pat. No. 4,820,626 issued Apr. 11, 1989, which are related to U.S. Pat. No. 4,994,387, which issued on Feb. 19, 1991, from application Ser. No. 07/210,218, filed Jun. 17, 1988, which is a continuation of Ser. No. 07/099,241, filed Sep. 21, 1987 now abandoned, which is a continuation of applications Ser. Nos. 06/848,913 and 06/848,917, both filed Apr. 7, 1986 and both now abandoned, which respectively, are continuations of applications Ser. No. 06/550,305, now abandoned filed Nov. 10, 1983, a portion of which is assigned to the assignee hereof and which application is hereby incorporated by reference as if fully set forth herein, and Ser. No. 06/550, 306, also filed Nov. 10, 1983, now abandoned. This application is also a continuation- in-part of U.S. Ser. No. 07/880,559 filed May 8, 1992, now abandoned, entitled, "A Method of Treating a Synthetic or Naturally Occurring Surface with a Collagen Laminate to Support Microvascular Endothelial Cell Growth and the Surface Itself", which is a divisional of U.S. Pat. No. 5,131,907 which issued Jul. 21, 1992 form U.S. Ser. No. 07/666,475 filed Mar. 6, 1991 which is a continuation of U.S. Ser. No. 06/848,453 filed Apr. 4, 1986, now abandoned, which is a continuation-in-part of U.S. Ser. No. 06/742,086 filed Jun. 6, 1985, now U.S. Pat. No. 4,820,626 which issued Apr. 11, 1989.

FIELD OF THE INVENTION

The present invention relates to the field of implantable prosthetic devices, or implants, for implantation into humans, and more particularly to synthetic implants such as vascular grafts which are commonly used to replace the large veins or arteries of human patients.

BACKGROUND OF THE INVENTION

The development of the idea of prosthetic vascular grafts has been a major goal of vascular surgery since the first grafts were used over 30 years ago. Most approaches have concentrated on creating a surface that is thromboresistant, with the majority of these efforts directed toward an improved polymer surface. Perhaps the ideal blood-surface interface is the naturally occurring human endothelium. If present on a prosthetic graft, it would offer many of the advantages of a native vessel. Unfortunately, endothelialization occurs only to a limited degree in prosthetic grafts when placed into humans, in contrast to animals where graft endothelialization does occur. Seeding endothelial cells onto preclotted prosthetic grafts prior to implantation has improved the endothelial cell coverage of grafts in animals, but this technique has had limited use in humans. See "Human Adult Endothelial Cell Growth in Culture", Bruce Jarrell, et al., *Journal of Vascular Surgery* 1984, I(6), 757–764; Herring et al., "A Single and Staged Technique for Seeding Vascular Grafts with Autogenous Endothelium", *Surgery* 1978, 84, 498–504; Graham et al., "Cultured Autogenous Endothelial Cell Seeding of Vascular Prosthetic Grafts", *Surg Forum* 1979, 30, 204–6; Graham et al., "Expanded Polytetrafluoroethylene Vascular Prostheses Seeded with Enzymatically Derived and Cultured Canine Endothelial Cells", *Surgery* 1982, 91, 550–9 and Dilley et al., "Endothelial Seeding of Vascular Prostheses", *Biology of Endothelial Cells, pp* 401–11, Jaffe ed., The Hague: Martinus Nijhoff, 1984.

Over the past three decades, artificial grafts have been used to provide immediate restoration of blood flow to areas of ischemia as a result of atherosclerotic vascular disease. In addition, they have been used to provide vascular access for hemodialysis in patients with chronic renal failure, and in the repair of arterial aneurysms. Although initially successful at restoring perfusion to ischemic tissues, the long-term prognosis for these grafts is not encouraging. Over an extended period, grafts less than 4 mm in diameter lose their patency as they become occluded via fibrin deposition and cellular adhesion. Dilley supra. This process appears to be secondary, and to be due in part to the thrombogenic nature of the nude (i.e., nonendothelialized) surface of the implanted prostheses. See Berger et al., "Healing of Arterial Prostheses in Man: It's Incompleteness", *Ann. Surg.* 1972, 175, 118–27. Thus, much current research is being aimed at either: (1) developing grafts with an artificial, nonthrombogenic surface, or (2) lining vascular prostheses with human endothelial cells, in the hope of producing a nonthrombogenic endothelial cell surface such as exists in native human vessels.

Endothelial cells from animal sources have been studied in culture since the 1920's. In 1973, Jaffe et al. successfully cultured endothelial cells from human umbilical veins and these cells have been characterized functionally. See Jaffe et al., "Synthesis of Antihemophilia Factor Antigen by Cultured Human Endothelial Cells", *J. Clin. Invest.* 1973, 55, 2757–64; Lewis, "Endothelium in Tissue Culture", *Am. J. Anat.* 1922, 30, 39–59; Jaffe et al., "Culture of Human Endothelial Cells Derived From Umbilical Veins", *J. Clin. Invest.* 1973, 52, 2745–56. These cell cultures demonstrate a growth potential, but the total number of cells produced from a single umbilical vein is usually quite limited, in the range of a 10–100-fold increase in harvested endothelial cells.

While several techniques have been proposed to increase the number of cells produced in the use of human umbilical vein endothelial cells, the ability to culture endothelial cells in large numbers remains less than ideal. Some investigators have had some success in culturing human adult endothelial cells from pulmonary arteries and veins, but only for short periods of time. It has also been shown that human iliac artery endothelial cells may be cultured for a short number of passages. In a study by Glassberg et al., for example, it is reported that 50 to 500 viable cells can be obtained per 5-inch vessel segment, a very low yield. "Cultured Endothelial Cells Derived From Human Iliac Arteries", *In Vitro* 1982, 18, 859–66. Fry et al. have reported successfully culturing human adult endothelial cells from abdominal arteries removed at the time of cadaver donor nephrectomy, but these cells also demonstrated early senescence.

It is apparent from existing techniques that it is difficult to produce enough cells to preendothelialize a graft with a reasonable amount of vessel from the donor patient. Rather than completely endothelializing a graft prior to implantation, the concept of subconfluent "seeding" of a preclotted graft developed. Seeding vascular grafts with autogenous endothelial cells has recently been shown to increase the rate of endothelial coverage of the grafts of experimental animals. See Herring et al. and Graham et al.

supra. Once covered by endothelium, grafts in dogs have been shown to be less thrombogenic as measured by platelet reactivity, to be more resistant to inoculation from bloodborn bacterial challenge, and to have prolonged patency of small-caliber vascular grafts. See Sharefkin et al., "Early Normalization of Platelet Survival by Endothelial Seeding of Dacron Arterial Prostheses in Dogs", Surgery 1982, 92, 385–93; Stanley et al., "Enhanced Patency of Small Diameter Externally Supported Dacron Iliofemoral Grafts Seeded with Endothelial Cells", Surgery 1982, 92, 994–1005; and Watkins et al., "Adult Human Saphenous Vein Endothelial Cells: Assessment of Their Reproductive Capacity for Use in Endothelial Seeding of Vascular Prostheses", J. Surg. Res. 1984, 36, 588–96.

A point of major concern when translating to human graft seeding has been the ability to produce enough endothelial cells with the use of human vascular tissue to allow seeding at a density high enough to attain endothelial coverage of the graft. Watkins et al., using human saphenous vein remnants following coronary artery bypass surgery were able to produce small quantities of endothelial cells in culture, and reported a low-fold increase in confluent cell area obtained in culture after 4 to 6 weeks. See Watkins et al. supra.

Even if it were possible to substantially expand the number of endothelial cells available through vigorous culturing techniques, concerns would still remain concerning the "health" of these endothelial cells after as many as 40 or 50 population doublings. Furthermore, the incubation of such cells in cultures which are foreign to their natural environment raises further concerns about genetic alterations and/or patient contamination with viruses, toxins or other damaging materials.

Many endothelialization procedures are suggested in the literature. Investigations in this area have been complicated by the diverse nature of the endothelium itself, and by the species to species differences which have been found relating to the behavior and characteristics of the endothelium. Fishman, "Endothelium: A Distributed Organ of Diverse Capabilities", Annals of New York Academy of Sciences 1982, 1–8; Sauvage et al., "Interspecies Healing of Porous Arterial Prostheses", Arch Surg. 1974, 109, 698–705; and Berger, "Healing of Arterial Prostheses in Man: Its Incompleteness", supra. Nonetheless, the literature is replete with reports of experiments involving the seeding of endothelial cells on various grafts, in various species, with a mixture of results. F. Hess et al., "The Endothelialization Process of a Fibrous Polyurethane Microvascular Prostheses After Implantation in the Abdominal Aorta of the Rat", Journal of Cardiovascular Surgery 1983, 24(5), 516–524); W. K. Nicholas et al., "Increased Adherence of Vascular Endothelial Cells to Biomer Precoated with Extracellular Matrix", Trans. Am. Soc. Artif. Intern Organs 1981, 28, 208–212; C. L. Ives et al., "The Importance of Cell Origin and Substrate in the kinetics of Endothelial cell Alignment in Response to Steady Flow", Trans. Am. Soc. Artif. Intern Organs 1983, 29, 269–274; L. M. Graham et al., "Expanded Polytetrafluoroethylene Vascular Prostheses Seeded with Enzymatically Derived and Cultured Canine Endothelial Cells", Surgery 1982, 91 (5), 550–559; S. G. Eskin et al., "Behavior of Endothelial Cells cultured on Silastic and Dacron Velour Under Flow conditions" In Vitro: Implications for Prelining Vascular Grafts wit Cells, Artificial Organs 1983, 7 (1), 31–37; T. A. Belden et al., "Endothelial Cell Seeding of Small-Diameter Vascular Grafts", Trans. Am. Soc. Artif. Intern. Organs 1982, 28, 173–177; W. E. Burkel et al., "Fate of Knitted Dacron Velour Vascular Grafts Seeded with Enzymatically Derived Autologous Canine Endothelium", Trans. Am. Soc. Artif. Intern. Organs 1982, 28, 178–182; M. T. Watkins et al., "Adult Human Saphenous Vein Endothelial Cells: Assessment of Their Reproductive Capacity for Use in Endothelial Seeding of Vascular Prostheses", Journal of Surgical Research 1984, 36, 588–596; M. B. Herring et al., "Seeding Arterial Prostheses with Vascular Endothelium", Ann. Surg. 1979, 190(1), 84–90; A. Wesolow, "The Healing of Arterial Prostheses—The State of the Art", Thorac. Cardiovasc. Surgeon 1982, 30, 196–208; T. Ishihara et al., "Occurrence and Significance of Endothelial Cells in Implanted Porcine Bioprosthetic Valves", American Journal of Cardiology 1981, 48, 443–454; W. E. Burkel et al., "Fate of Knitted Dacron Velour Vascular Grafts Seeded with Enzymatically Derived Autologous Canine Endothelium", Trans. Am. Soc. Artif Intern Organ 1982, 28, 178–182.

It has been previously recognized that human microvascular endothelial cells, that is, the cells which are derived from capillaries, arterioles, and venules, will function suitably in place of large vessel cells even though there are morphological and functional differences between large vessel endothelial cells and microvascular endothelial cells in their native tissues.

U.S. Ser. No. 725,950, filed Jun. 27, 1991, described the treatment to confluence of a vascular graft or other implant using microvascular endothelial cells which are separated from fat which is obtained at the beginning of an uninterrupted surgical procedure. Fat tissue is removed from the patient after sterile conditions have been established. Microvascular endothelial cells in that fat are then quickly separated from their related tissue by enzymatic digestion and centrifugation, and the cells are deposited on a surface by gravity or by filtration, which surface is then implanted in the patient during the latter stages of the same operation.

Notwithstanding the work reported in this field, a need still exists for improved grafts, simple, reliable procedures which can successfully endothelialize the surfaces of human implants such as surfaces of vascular grafts, and for other methods of vascularization.

SUMMARY OF THE INVENTION

The present invention provides improved implants.

Improved methods of preparing endothelialized implants are also provided.

In some embodiments of the present invention, improved implants have porosity sufficient to allow the surface of the implants to be used as filters. Endothelial cells may be deposited in pores of implants in other aspects of the invention.

In other embodiments of the present invention, an implant has a surface rich in amines.

In still other embodiments of the present invention microvascular rich fat tissue is obtained from the patient and homogenized to form a cellular slurry. The cellular slurry may then be applied onto an implant. Implants so prepared are provided in some aspects of the present invention.

These and other aspects of the present invention will become apparent from the following, more detailed description.

DESCRIPTION OF THE PREFERRED EMBODIMENT

The preferred embodiments of the present invention stems from work to improve vascular implants. Earlier work was aimed at either: (1) developing implants with an artificial, non-thrombogenic surface, or (2) lining vascular prostheses with human endothelial cells, in the hope of producing a non-thrombogenic endothelial cell surface such as exists in native human vessels.

The present invention provides improved implants which facilitate deposition of endothelial cells in suspension and reduce thrombogenicity of implants. Implants encompassed by the present invention include, but are not limited to, for example, intravascular devices such as artificial vascular prostheses, artificial hearts, and heart valves. It is anticipated that the herein described procedures may lead to the development of other artificial organs or devices. These organs and devices will receive circulating blood either following implantation or in an extracorporeal circuit, and the present procedures provide a non-thrombogenic or anti-thrombogenic interface between the blood and the implanted surface.

In some embodiments of the present invention novel implants may be made from implant material having porosity. Such porosity may provide a filtering function, facilitating deposition of cells suspended in aqueous solution on the implant surface and within the pores of the implant. Furthermore, cells deposited within the pores of the implant by deposition, or by other processes, may not initially be in contact with blood flow, thus reducing thrombogenicity of the implant.

The implants may be polymeric or natural material ranging in porosity from about 1 to about 20 microns. For example, implant material can be a polymer such as polyester polytetrafluoroethylene, or a naturally occurring material such as an umbilical vein, saphenous vein, or native bovine artery.

Figure 1:
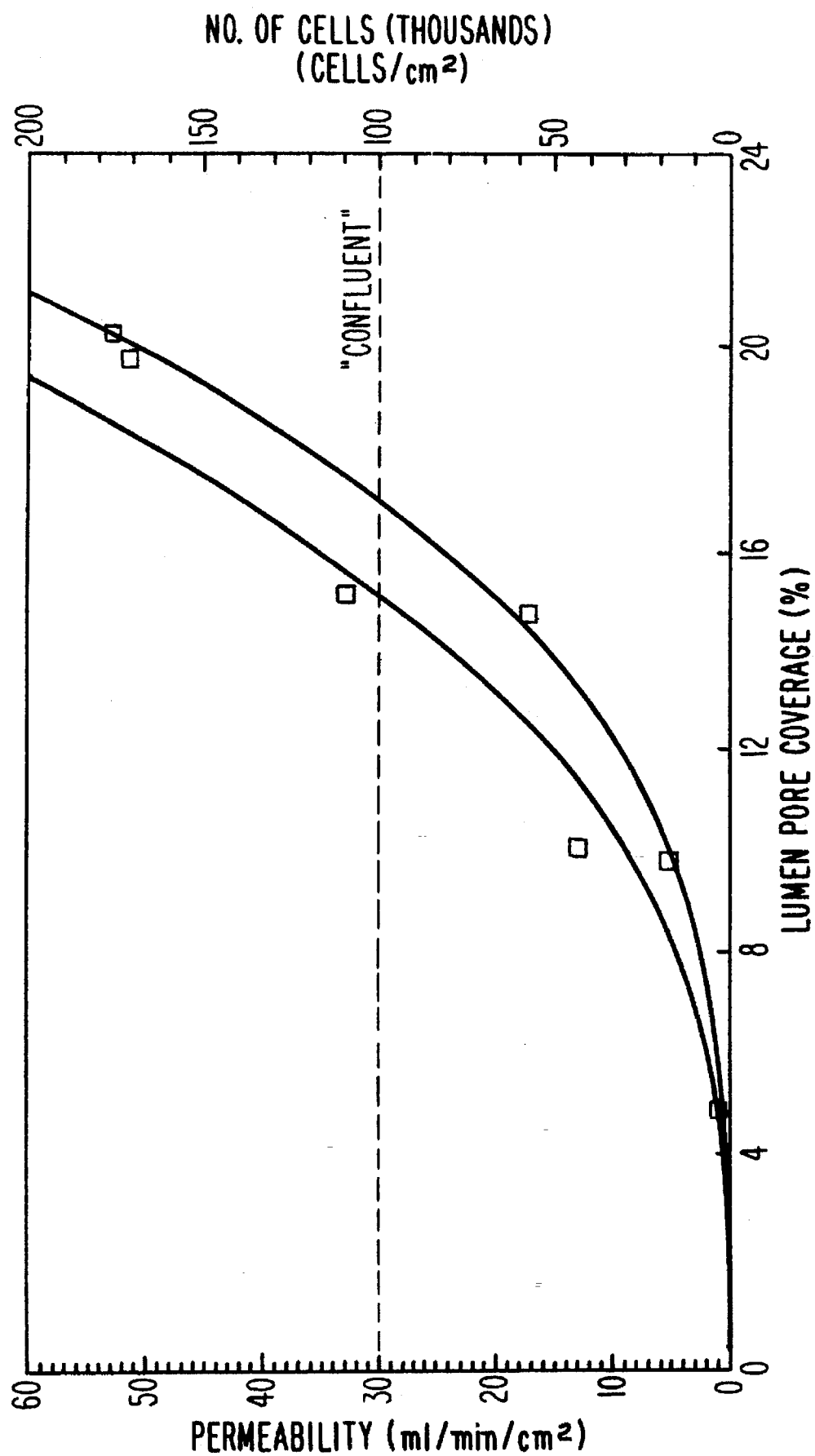
FIG. 1 is a schematic representation of the effect of permeability and pore coverage of an implant on cell deposition on the implant surface.

It is preferable in some aspects of the present invention to optimize water flow-through characteristics. As shown in FIG. 1, the deposition of endothelial cells onto the surface of implant material is increased when the implant has significant water flow through characteristics. Implants having flow through characteristics useful to allow the surface of the implant to be used as a filter generally having porosity of from about 1 to about 4 microns. Optimally, an implant will have a permeability of at least about 10 ml/min/cm². In preferred embodiments of the present invention, permeability will range from about 10 ml/min/cm² to about 40 ml/min/cm². Pore coverage may optimally be at least about 8%. In preferred embodiments of the present invention, pore coverage is from about 12% to about 16%. In other embodiments, implants may have at least some porosity of from about 10 to about 20 microns in which endothelial cells may be deposited. Treatment of the implant with a surface such as a protein surface or upon surfaces which have been modified to emulate protein surfaces are also preferred.

Novel implants of the present invention may have an amine rich surface. The amine rich surface is, of course, inclusive of the pore surfaces which, while distinguishable from the implant surface, are exposed to the external environment, be it cell culture, blood, or other substances.

Figure 2:
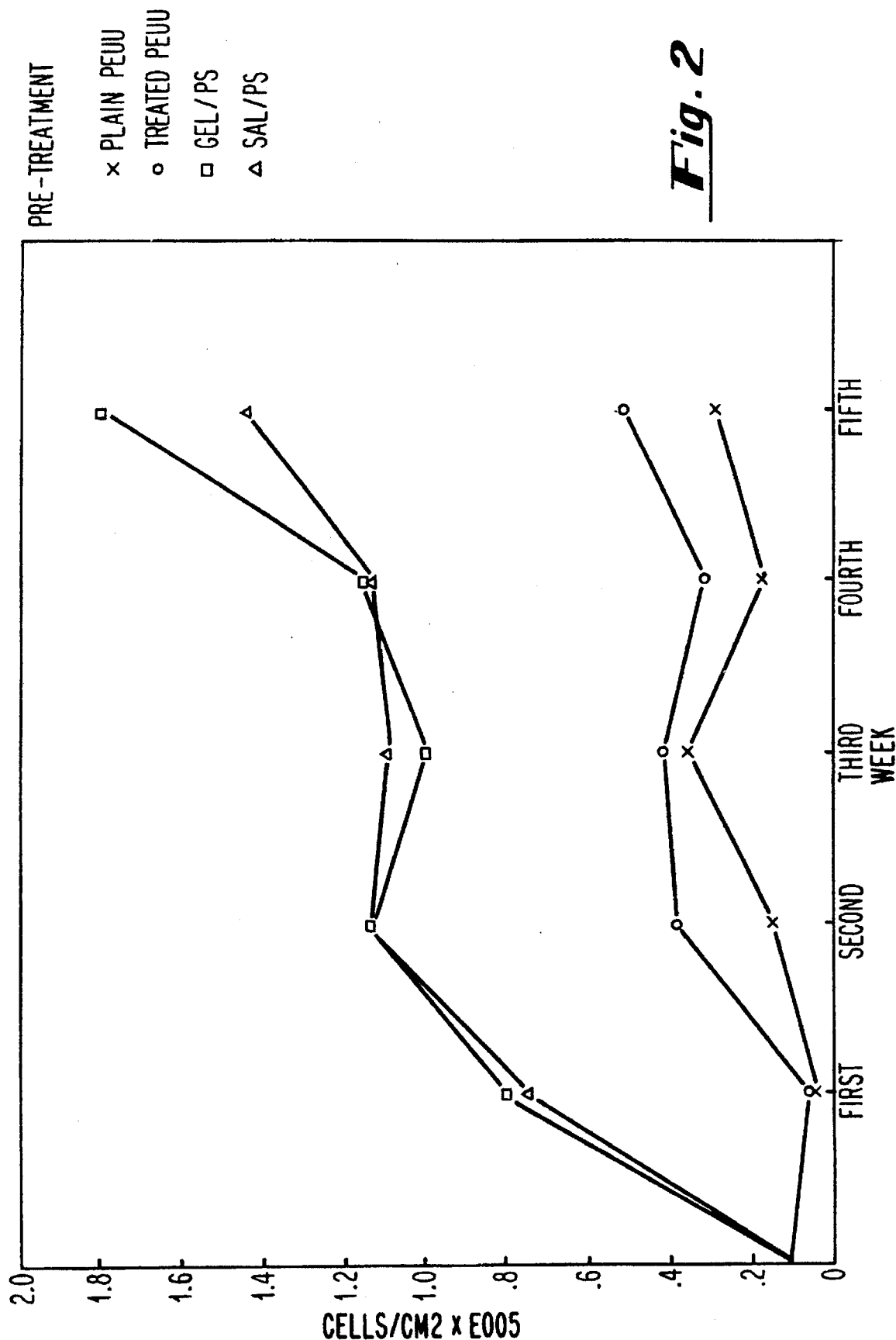
FIG. 2 illustrates the rate of cell proliferation for cell cultures on four different surfaces, gelatin coated polystyrene, saline coated polystyrene, untreated polyurethane and glow-discharge plasma treated polyurethane.

It has been shown that endothelial cells exhibit reduced thrombogenicity when in contact with different matrix proteins of the basement membrane as compared to tissue collagen. For example, the growth of endothelial cells was reduced when cells were placed on surfaces containing type IV/V collagen, the surface cells normally reside on, as compared to type I/III collagen. Madri and Williams, *J. Cell Biol.* 1983, 97, 153. In some embodiments of the present invention, implant material such as commercially available polymer implant material, may be treated by glow-discharge plasma modification to provide a surface having properties similar to basement membrane. For example, polyurethane vascular grafts may be glow-discharge plasma modified (*Plastics*, 85, Proceedings of the SPE 43rd Annual Technical Conference and Exhibition pp. 685–688 (1985)) using tubular geometric technology of the Becton-Dickinson Company (Franklin Lakes, N.J.) to produce a surface chemistry on the inside of a tubular graft which is rich in amines, similar to basement membrane. An amine rich surface is a surface which has an amine content similar to the amine content of basement membrane. Of course, more or less amine content is permissible as long as the desired characteristics are retained. For example, an amine-rich surface has increased adhesiveness to microvascular endothelial cells as compared to untreated implants and is amenable to the long term establishment of endothelial cell monolayers. FIG. 2 illustrates that a treated polyurethane surface showed minimal proliferation as compared to an untreated polyurethane surface. Furthermore, the treated surface exhibits reduced adherence of platelets and coagulation proteins and reduced thrombogenicity. Such implants may be implanted with or without prior treatment with endothelial cells such as microvascular endothelial cell treatment described herein or in Ser. No. 725,950, filed Jun. 27, 1991. Preferably, glow-discharge plasma modified implants are pre-treated with microvascular endothelial cells prior to implantation. Thus, novel implants of the present invention may be glow-discharge plasma treated and/or may have porosity to enhance adherence of endothelial cells and reduce thrombogenicity.

Figure 3A:
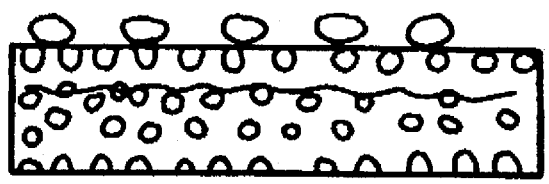
FIG. 3 is a schematic representation of cell deposition as a result of gravity (FIG. 3A) using a non-permeable implant and as a result of flow-through filtration (FIG. 3B) using a permeable implant. In each case, porosity equals 1–4 microns.
Figure 3B:
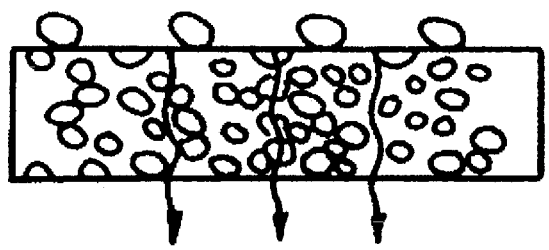

In some embodiments of the present invention, the porous implant material, which has preferably been glow-discharge plasma treated, may be useful as an implant such as a vascular graft. In such embodiments of the present invention, endothelial cells are deposited on the surface and/or within the pores of the porous implant material by means of filtration action, as illustrated in FIG. 3, wherein an aqueous phase containing endothelial cells is passed through the porous implant, leaving behind cells deposited on the surface and/or in the pores below the lumenal surface of the implant. Of course, cell adherence to the surface and within the pores of the implant will be enhanced by the use of novel implant material of the present invention having an amine-rich surface. In some embodiments of the present invention, the surface of the vascular graft may be treated with a surfactant or cleaning agent to make it more easily wettable.

Endothelial cells suspended in an aqueous phase are preferably microvascular endothelial cells isolated and prepared as described in Ser. No. 725,950, filed Jun. 27, 1991, and incorporated by reference herein in its entirety. Endothelial cells may be deposited on the implant by suspending the isolated endothelial cells in a buffered saline which contains plasma-derived protein from the patient. The protein solution is prepared by mixing six parts buffered solution with one part plasma to produce a solution which contains approximately one percent (1%) protein. Albumin is the preferred source of the protein, but non-plasma sources of protein can be used. The microvascular endothelial cell suspension is then preferably pelletized by centrifugation (200×g) and the pellet resuspended with protein containing buffer solution. This resuspension should be performed at a ratio of approximately 1:5 to 1:15 or about 1:10 volumes of packed microvascular endothelial cells to buffer solution. The cell suspension is filtered through the surface to provide a layer of endothelial cells on the surface and within the pores of the implant to be treated. Time needed for adherence of the cells to the surface and within the pores of the implant will vary depending upon the implant material and any pretreatments the implant may have received. For example, endothelial cells will adhere to an untreated polyester graft surface in two hours, while pretreatment of the polyester graft with protein reduces the time for adherence to approximately ten minutes. It is expected that endothelial cells will adhere at least as well to implant material having a surface rich in amines and which has a sufficient flow through characteristics. Following incubation for a sufficient time, the implant is washed with a protein containing buffer. The implant may now be implanted in a normal manner.

The porous implant material may also be useful to provide vascularization without the use of a vascular graft. In such embodiments, implant material is treated with endothelial cells by filtration or by simple deposition such that the endothelial cells are deposited within the pores of the implant material as described above and the implant is implanted in a normal manner. Vascularization is accomplished by engrowth of surrounding endothelial cells with transplanted cells from the new vascular conduit.

In some embodiments of the present invention, endothelial cells deposited in the pores of the implant may be transformed to have desired biological properties. For example, said endothelial cells may be transformed with a gene for a heterologous protein useful as a therapeutic agent, such as a gene coding for plasminogen activator, soluble CD-4, Factor VIII, Factor IX, von Willebrand Factor, urokinase, hirudin, interferons, tumor necrosis factor, interleukins, hematopoietic growth factor, antibodies, glucocerebrosidase, ADA, phenylalanine, hydroxylase, human growth hormone, insulin and erythropoietin. Endothelial cells may be transformed by genes coding for therapeutic agents by methods known to those skilled in the art. Gene, when used herein, is intended to connote the common meaning of the word, i.e. a DNA or RNA sequence which encodes a functional protein or RNA molecule. Genes of the present invention may be synthetic or naturally occurring.

Tranformation is the process by which cells have incorporated an exogenous gene by direct infection, transfection or other means of uptake. In preferred embodiments of the present invention, transformation is accomplished by means of a liposome-mediated transfection as described in Ausubel, et al., *Current Protocols in Molecular Biology* (1991) incorporated by reference herein in its entirety. A gene coding for a therapeutic agent is incorporated into a suitable vector such as pSG5 (Stratagene Cloning Systems, La Jolla, Calif.). Other vectors having characteristics useful in the present invention will be apparent to those skilled in the art. The term "vector" is well understood in the art and is synonymous with the phrase "cloning vehicle". A vector carrying one or more desired genes may be used to transform endothelial cells of the present invention by standard procedures known in the art.

In other aspects of the present invention, implants, such as those of the present invention, may be treated with endothelial cells by improved methods using microvascular fat tissue which do not require isolation of endothelial cells from the fat tissue.

Microvascular fat provides a rich source of endothelial cells for treatment of implant material. For example, 20 grams of the patient's fat will provide ample endothelial cells to treat a surface area of one hundred and eighty square centimeters (180 cm$^2$), the surface area represented by a "typical" femoral artery to popliteal artery bypass graft. In accordance with methods of the invention fat tissue is obtained from a patient under sterile conditions and homogenized to form a cellular slurry. The fat tissue may be homogenized by any of the methods known to those skilled in the art. For example, the fat tissue may be blenderized or may be extruded. Homogenized fat tissue, or cellular slurry, is a smooth mixture in which tissue components, and especially microvascular endothelial cells, are uniformly distributed. The cellular slurry may then be applied to an implant, such as novel implants of the present invention which have porosity/and or an amine rich surfaces, thereby eliminating the need for isolation of microvascular endothelial cells.

As observed in Ser. No. 725,950, filed Jun. 27, 1991, microvascular endothelial cells can be gelled within a protein meshwork, and following incubation in culture media, will migrate to the surface of the gel. This has been confirmed from scanning electron micrographs which show human microvascular endothelial cells forming a confluent monolayer on the surface of a polyester graft after these cells were preclotted in human plasma. It is, therefore, believed that endothelial cells in a cellular slurry will migrate to the surface of the slurry to form a monolayer on an implant surface. Furthermore, other components within the slurry will enhance the growth and adherence of the cells on and/or within the implant. In some aspects of the invention, a vital dye such as methylene blue or cardio green can be added to the cellular slurry for visualization to insure even distribution of the endothelial cells on the implant. Methods of applying the cellular slurry will be apparent to one skilled in the art in light of the present disclosure. For example, the cellular slurry may be applied via sterile swab or spatula.

In preferred embodiments of the present invention, the cellular slurry is applied to the implant so as to result in at least 50% confluence of endothelial cells on and/or in the pores of the implant. The ability to treat an implant surface with 100% confluence of endothelial cells is desirable. However, 50% confluence is acceptable, as it requires the cells to duplicate only once to create a confluent cell layer. Thereafter, the implant may be implanted in accordance with standard procedures.

Those of ordinary skill in the art will further recognize that various departures can be made from the methods and procedures described herein without departing from the scope of the present invention, which is defined more particularly in the examples and claims appended hereto.

The following examples are provided for illustrative purposes only and are not intended to limit the invention.

EXAMPLES

EXAMPLE 1

Filtration Characteristics of Porous Implants

Microvascular endothelial cell suspension in Medium 199E containing serum proteins is contacted with a range of porous implants to determine the optimal porosity to achieve confluence. The results are shown in FIG. 1 wherein 50% confluence (cells/cm$^2$) is achieved when the implant has a permeability of about 15 ml/min/cm$^2$ and when the lumen pore coverage ranges from about 12% to about 14%. 100% confluence is achieved at approximately 30 ml/min/cm$^2$ when the lumen pore coverage is from about 15% to about 17%.

EXAMPLE 2

Growth Adherence of Large Vessel Endothelial Cells (LVEC) to Plain and Treated Polyurethane and Gelatin and Saline Coated Polystyrene LV endothelial cells were suspended in 15% fetal bovine serum in Medium 199E and added to four different surfaces, an untreated polyurethane surface (X), a glow discharge treated polyurethane surface which had a surface rich in amines (o), an untreated polystyrene surface (□), and a collagen coated polystyrene surface (Δ). Cells were incubated on the surfaces and rates of growth were observed. Cells grown on collagen coated polystyrene had the highest rate of growth (0.1 cells/cm$_2$×10$^5$ in the first week, to 1.8 cells/cm$_2$×10$^5$ in the fifth week). Growth rates were substantially lower for cells grown on polyurethane surfaces (0.5 cells/cm$_2$×10$^5$ in the fifth week) and still lower for cells grown on polyurethane surfaces rich in amines (0.25 cells/cm$_2$×10$^5$ in the fifth week).

What is claimed is:

1. An implant having a lumen, the implant consisting essentially of implant material having a surface porosity of from about 1 to about 20 microns and a permeability of about 10 ml/min/cm$^2$ to about 40 ml/min/cm$^2$ wherein endothelial cells are deposited in pores of about 10 to about 20 microns of the implant material by forced deposition.

2. The implant of claim 1 in which the lumenal surface of the implant has porosity of from about 1 to about 4 microns.

3. The implant of claim 1 wherein the implant has a percent pore coverage of at least 8%.

4. The implant of claim 3 wherein the percent of pore coverage is from 12% to 16%.

5. The implant of claim 1 wherein microvascular endothelial cells are deposited on the implant surface.

6. The implant of claim 5 wherein said endothelial cells are transformed with a gene coding for a therapeutic agent selected from the group consisting of plasminogen activator, soluble CD-4, Factor VIII, Factor IX, yon Willebrand Factor, urokinase, hirudin, interferons, tumor necrosis factor, interleukins, hematopoietic growth factor, antibodies, glucocerebrosidase, ADA, phenylalanine, hydroxylase, human growth hormone, insulin and erythropoietin.

\* \* \* \* \*